United States Patent [19]
Adahan

[11] Patent Number: 4,739,791
[45] Date of Patent: Apr. 26, 1988

[54] FLUID COLLECTION CONTAINER PARTICULARLY USEFUL IN SUCTION PUMPS

[76] Inventor: Carmeli Adahan, 1316/02 Ramot 03, Jerusalem 97 725, Israel

[21] Appl. No.: 30,809

[22] Filed: Mar. 26, 1987

[51] Int. Cl.$^4$ .............................................. F16K 17/06
[52] U.S. Cl. .................................... 137/205; 137/202; 137/592
[58] Field of Search ................ 137/205, 202, 592, 389

[56] References Cited
U.S. PATENT DOCUMENTS

| | | | |
|---|---|---|---|
| 2,317,589 | 4/1943 | Collinson | 137/205 X |
| 2,602,465 | 7/1952 | Goehring | 137/592 X |
| 3,280,858 | 10/1966 | Paulson | 137/205 X |
| 3,726,303 | 4/1973 | Allen | 137/205 |

*Primary Examiner*—Alan Cohan
*Attorney, Agent, or Firm*—Benjamin J. Barish

[57] ABSTRACT

A fluid collection container formed in its top wall with a fluid inlet port connectable to a source of the fluid to be collected, and a suction port connectable to a suction source. A closure member is normally disposed in an open position spaced below the suction port but is movable to a closed position against the suction port when the container is full, to prevent passage of fluid from the container to the suction source. The closure member is supported on a stem carried by a release button passing through an opening in the top wall of the container adjacent to but laterally of the suction port. The stem passes through an opening in the closure member and is formed with an enlargement at its lower end normally supporting the closure member in its open position spaced below the suction port. The release button includes a further enlargement normally spaced above the closure member but movable against it, upon depression of the release button when the closure member is in its closed position against the suction port, to move the closure member to its open position spaced below the suction port.

15 Claims, 1 Drawing Sheet

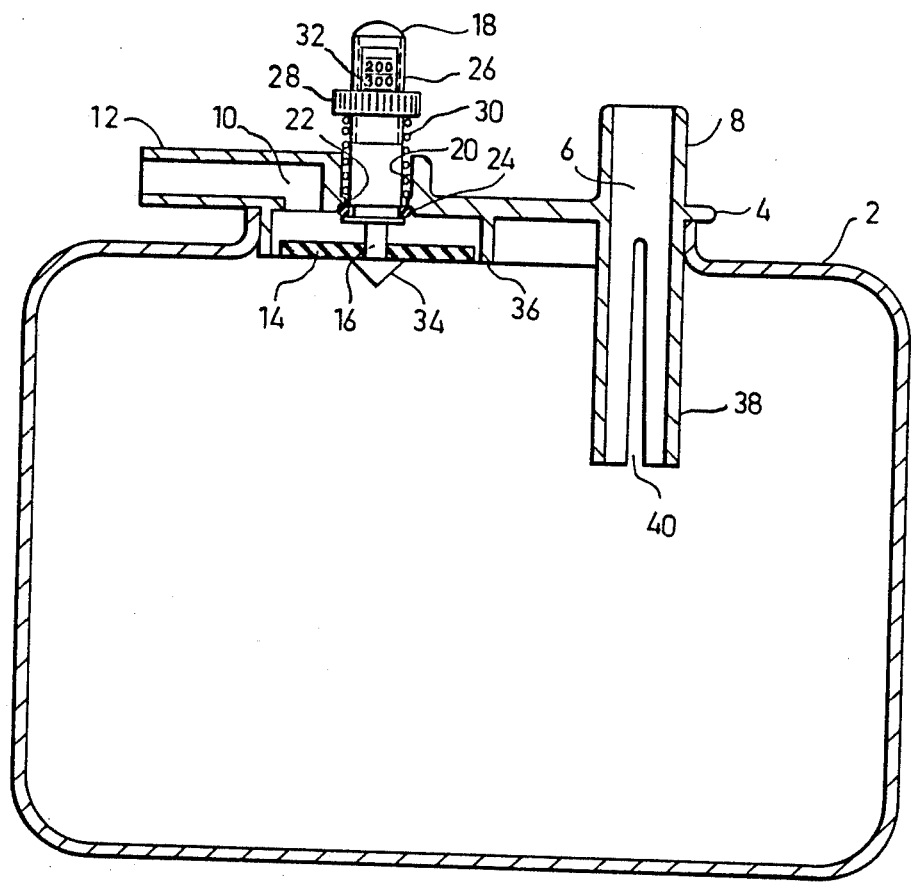

FLUID COLLECTION CONTAINER PARTICULARLY USEFUL IN SUCTION PUMPS

RELATED APPLICATIONS

The present application is related to my U.S. patent application No. 06/833,195, filed Feb. 27, 1986 for: Portable Fluid Pumping Device, and also to my U.S. patent application No. 07/030,808 for: Rolling Diaphragm Construction and Piston-Cylinder Assembly Particularly Useful for Suction or Compression Pumps, filed the same day as this application.

BACKGROUND OF THE INVENTION

The present invention relates to fluid collection containers, particularly useful in suction pumps for drawing off waste fluids, such as used in medical applications.

Fluid collection containers are commonly provided in suction pumps used for medical applications, wherein suction is applied to a catheter or tube in order to draw out fluids and to collect therein the fluid collection container. Such containers usually include an overflow protector which prevents fluid from passing from a full container to the suction pump, and an adjustable vacuum regulator which limits the suction to a desired level. However, most such overflow protectors now in use include floats which are of large volume, and which frequently require disassembly of the container in order to release the float once it has moved to its closed position. In addition, most such vacuum regulators now in use employ a gauge which displays the vacuum level, and a separate regulator which blocks the fluid flow when the vacuum exceeds a predetermined level.

An object of the present invention is to provide a fluid collection container providing overflow protection and vacuum regulation having advantages in the above respects.

BRIEF SUMMARY OF THE INVENTION

According to the present invention, there is provided a fluid collection container including a top wall formed with a fluid inlet port connectable to a source of the fluid to be collected, and a suction port connectable to a suction source; and a closure member normally disposed in an open position spaced below the suction port but movable to a closed position against the suction port when the container is full, to prevent passage of fluid from the container to the suction source. The closure member is supported on a stem carried by a release button passing through an opening in the top wall of the container adjacent to but laterally of the suction port. The stem passes through an opening in the closure member and is formed with an enlargement at its lower end normally supporting the closure member in its open position spaced below the suction port.

The release button includes a further enlargement normally spaced above the closure member but movable against it, upon depression of the release button when the closure member is in its closed position against the suction port, to move the closure member to its open position spaced away from the suction port.

In addition, in the described preferred embodiment the further enlargement carried by the release button is a valve member normally closing the opening in the top wall of the container. The release button further includes a spring normally urging the valve member to close the latter opening but permitting the valve member to move into the container to open the latter opening when the vacuum in the container exceeds a predetermined value. More particularly, the opening is formed with an annular internal rib, and the valve is in the form of a sealing ring carried by the release button and disposed inwardly of the annular internal rib. The release button further includes a threaded member threaded thereon outwardly of the sealing ring, and a spring interposed between the annular internal rib and the threaded member urging the sealing ring against the inner side of the annular rib according to the force of the spring as preset by the threaded member.

In the described preferred embodiment, the release button carries indicia indicating the predetermined level of vacuum which will cause the sealing ring to open the opening as preset by the position of the threaded member; also, the closure member is a sealing disc, and the container is a bottle having an upper open end, the top wall of the container being a cover removably attached to the upper open end of the bottle.

According to another feature in the described preferred embodiment, the fluid inlet port is connected to a tube extending externally of the bottle to direct inletted liquid downwardly therethrough while minimizing splash, the tube being formed with a slot extending lengthwise of the tube enabling air in the inletted fluid to enter the bottle without bubbling through the liquid therein.

It will thus be seen that a fluid collection container constructed in accordance with the foregoing features provides a number of important advantages. Thus, it prevents overflow from a filled container into the suction source. In addition, it provides a quick and convenient manner of releasing the overflow control member. Further, it limits the vacuum within the container to a predetermined maximum level, displays that limit, and permits convenient presetting of the limit. Still further, it minimizes splash which might inadvertently trigger the overflow member to close.

Further features and advantages of the invention will be apparent from the description below.

BRIEF DESCRIPTION OF THE DRAWINGS

The invention is herein described, by way of example only, with reference to the single attached drawing FIG. 1 illustrating a preferred embodiment of the invention.

DESCRIPTION OF A PREFERRED EMBODIMENT

The fluid collection container illustrated in the drawings comprises a bottle 2, having an open upper end closed by a cover, generally designated 4, which sealingly closes the upper open end of the bottle. The bottle is normally disposed in the position illustrated in FIG. 1 wherein cover 4 serves as the top wall of the bottle.

Cover 4 is formed with a fluid inlet port 6 connectable by a connector 8 to a source of the fluid to be collected. For example, if the device is used in a medical application, connector 8 of inlet port 6 might be connected to a drainage tube or a catheter. Cover 4 is further formed with a suction port 10 connectable by a connector 12 to a source of suction, for example a vacuum pump (not shown), such that when the vacuum pump is operated, a suction is produced within bottle 2 to draw fluid thereinto via inlet port 6.

Bottle 2 further includes a closure member 14, in the form of a sealing disc, which is normally supported in an open position spaced below the suction port 10 (as illustrated in the drawings), but movable against the suction port when the bottle is full of fluid to prevent passage of fluid from the bottle to the suction source. Sealing disc 14 may be lighter than the fluid to be collected in the bottle so as to float thereon; alternatively, it may be slightly heavier than the fluid such that the suction force applied via suction port 10, combined with the decrease in its weight when submerged in the fluid within bottle 2, will be sufficient to move it upwardly to its closed position against the suction port 10.

Sealing disc 14 is supported at the end of a stem 16 carried at the inner end of a release button 18 passing through a further opening 20 formed in the bottle cover 4. The latter opening 20 is integrally formed with an internal annular rib 22. Release button 18 passes through the cover opening 20 and carries a valve member in the form of a sealing ring 24 which normally bears against the inner surface of annular rib 22 and thereby closes its opening 20.

The outer face of release button 18 is threaded, as shown at 26, and receives a threaded nut 28. A coil spring 30 is interposed between nut 28 and annular rib 22, so as to urge release button 18 upwardly, whereby its sealing ring 24 seats firmly against annular rib 22 to close opening 20.

The force exerted by spring 30 on release button 18 to close opening 20 determines the maximum suction level within bottle 2. Thus, so long as the suction level is below this maximum value, sealing ring 24 of release button 18 closes opening 20; but when the suction level exceeds the maximum value fixed by spring 30, the suction draws in release button 18 to cause its sealing ring 24 to unseat from annular rib 22. This exposes the interior of the bottle to the atmosphere until the suction in the bottle drops to the maximum level, whereupon ring 30 moves release button 18 outwardly to cause its sealing spring 24 to reclose opening 20.

This maximum level of suction to be permitted within bottom 2 may be preset by threading nut 28 inwardly to increase the maximum level, or outwardly to decrease it. The outer end of release button 18 carries indicia 32, which thereby displays the maximum preset level of vacuum within bottle 2 by the position of nut 28 with respect to this indicia.

The outer diameter of stem 16 carried at the inner end of release button 18 is slightly smaller than the opening through sealing disc 14, so that the sealing disc is freely movable up and down with respect to the stem. The inner tip of stem 16 is formed with an enlargement 34 to support sealing disc in its lower, open position with respect to suction port 10. As shown in the drawing, enlargement 34 is pointed at its outer tip to permit the stem to be easily passed through the opening in the sealing disc 16.

The inner face of cover 4 is further formed with an internal annular rib or skirt 36 circumscribing both the suction port 10 and the sealing disc 14. This annular skirt serves as a splash guard which prevents liquid drops from splashing past sealing disc 16 into suction port 10, particularly when the fluid flow is high.

In addition, the fluid inlet port 6 is connected to a tube 38 extending internally of the bottle to direct the liquid drawn through the inlet port downwardly towards the bottom of the bottle so as to minimize splash. Tube 38 is formed with a slot 40 extending continuously for substantially the complete length of the portion of the tube within the container, enabling air in the inletted fluid to enter the bottle without bubbling through the liquid therein when the liquid level in the bottle is higher than the lower end of tube 38. Without slot 40, the air flow would create considerable turbulence in the fluid, and could cause sealing disc 14 to move to its closed position against suction port 10 before the bottle has been filled.

The illustrated fluid collection container operates as follows:

First, nut 28 is preset on release button 18 according to the maximum level of vacuum desired within the bottle 2. This maximum vacuum level is indicated by the position of nut 28 with respect to indicia 32.

The fluid inlet port 6 is then connected to the source of fluid to be collected in the bottle; and the suction port 10 is then connected, via connector 12, to the source of suction, e.g., a vacuum pump. The suction source removes the air from the interior of bottle 2, thereby producing a vacuum therein, which vacuum draws the fluids into bottle 2 via the fluid inlet port 6. Liquids which are drawn into the bottle pass downwardly through feed tube 38 so as to minimize splash, and air or other gas drawn into the bottle also passes through tube 38 but enters the bottle through the longitudinal slot 40. Thus, when the level of the liquid within the bottle rises to above the lower end of tube 38, slot 40 permits the air to pass into the bottle without bubbling through the liquid, which might produce splash.

During the filling of the bottle, sealing disc 14 is supported in its lower position spaced below the suction port 10. However, as the liquid level within the bottle rises to that of sealing disc 14, the suction force applied against the upper face of sealing disc 16 from suction port 10, combined with the buoyancy force produced on the sealing disc, causes the sealing disc to move upwardly to close the suction port 10, and thereby to prevent any fluid collected within the bottle 2 from passing to the suction source. During the filling of the bottle, annular skirt 36 shields the suction port 10 and sealing disc 14 from splash which might inadvertently cause the sealing disc to move towards its upper closed position closing suction port 10.

If sealing disc 14 has been inadvertently closed, for example by tilting the bottle, it is only necessary to depress the release button 18, whereupon its sealing ring 24 will move downwardly against the upper surface of sealing disc 14 and move it away from the suction port 10. If the vacuum within bottle 2 rises above a predetermined maximum value, the suction force will be applied against the inner face of sealing ring 24 of release button 18, moving the release button inwardly against the action of spring 30, to thereby connect the interior of the bottle to the atmosphere. The vacuum within the bottle will then immediately stop rising at the predetermined maximum value.

While the invention has been described with respect to one preferred embodiment, it will be appreciated that many variations, modifications and other applications of the invention may be made.

What is claimed is:

1. A fluid collection container including a top wall formed with a fluid inlet port connectable to a source of the fluid to be collected, and a suction port connectable to a suction source; and a closure member normally disposed in an open position spaced below the suction port but movable to a closed postion against the suction port when the container is full, to prevent passage of fluid from the container to the suction source; characterized in that said closure member is supported on a stem carried by a release button passing through an opening in said top wall of the container adjacent to but laterally of said suction port, said stem passing through an opening in said closure member and being formed with an enlargement at its lower end normally supporting the closure member in its open position spaced below said suction port; said release button including a further enlargement normally spaced above said closure member but movable against it, upon depression of the release button when the closure member is in its closed position against the suction port, to move the closure member to its open position spaced below the suction port.

2. The fluid collection container according to claim 1, wherein said further enlargement of said release button is a valve member normally closing said opening in the top wall of the container, said release button further including a spring normally urging said valve member to close said latter opening but permitting the valve member to move into the container to open said latter opening when the vacuum in said container exceeds a predetermined level.

3. The fluid collection container according to claim 2, wherein said opening in the top wall of the container is formed with an annular internal rib, said valve member including a sealing ring carried by said release button and disposed inwardly of said annular internal rib, said release button further including a threaded member threaded thereon outwardly of said sealing ring, and a spring interposed between said annular internal rib and said threaded member urging said sealing ring against the inner side of said annular rib according to the force of said spring as preset by said threaded member.

4. The fluid collection container according to claim 3, wherein said release button further includes indicia indicating the predetermined level of vacuum which will cause said sealing ring to open said opening as preset by the position of said threaded member.

5. The fluid collection container according to claim 1, wherein said enlargement at the lower end of said stem is pointed at its outer tip to facilitate passing it through said opening in the closure member.

6. The fluid collection container according to claim 1, wherein said closure member is a sealing disc, and said container is a bottle having an upper open end, said top wall of the container being a cover removably attached to the upper open end of the bottle.

7. The fluid collection container according to claim 6, wherein said cover further includes an annular skirt on its inner face circumscribing said suction port and said sealing disc.

8. The fluid collection container, according to claim 6, wherein said fluid inlet port is connected to a tube extending internally of the bottle to direct inletted fluid downwardly therethrough while minimizing splash, said tube being formed with a slot extending lengthwise of the tube enabling air in the inletted fluid to enter the bottle without bubbling through the fluid therein.

9. A fluid collection container including a cover removably attached to the container and including a fluid inlet port connectable to a source of the fluid to be collected, a suction port connectable to a suction source, and a sealing disc normally disposed in an open position spaced below the suction port but movable to a closed position against the suction port when the container is full, to prevent passage of fluid from the container to the suction source, said sealing disc being supported on a stem carried by a release button passing through an opening in said top wall of the container adjacent to but laterally of said suction port, said stem passing through an opening in said sealing disc and being formed with an enlargement at its lower end normally supporting the sealing disc in its open position spaced below said suction port; said release button including a further enlargement normally spaced above said sealing disc but movable against it, upon depression of the release button when the sealing disc is in its closed position against the suction port, to move the sealing disc to its open position spaced below the suction port.

10. The fluid collection container according to claim 9, wherein said further enlargement of said release button is a valve member normally closing said opening in the top wall of the container, said release button further including a spring normally urging said valve member to close said latter opening but permitting the valve member to move into the container to open said latter opening when the vacuum in said container exceeds a predetermined level.

11. The fluid collection container according to claim 10, wherein said opening in the top wall of the container is formed with an annular internal rib, said valve member including a sealing ring carried by said release button and disposed inwardly of said annular internal rib, said release button further including a threaded member threaded thereon outwardly of said sealing ring, and a spring interposed between said annular internal rib and said threaded member urging said sealing ring against the inner side of said annular rib according to the force of said spring as preset by said threaded member.

12. The fluid collection container according to claim 11, wherein said release button further includes indicia indicating the predetermined level of vacuum which will cause said sealing ring to open said opening as preset by the position of said threaded member.

13. The fluid collection container according to claim 9, wherein said enlargement at the lower end of said stem is pointed at its outer tip to facilitate passing it through said opening in the sealing disc.

14. The fluid collection container, according to claim 9, wherein said cover further includes an annular skirt on its inner face circumscribing said suction port and said sealing disc.

15. A fluid collection container including a top wall formed with a fluid inlet port connectable to a source of the fluid to be collected, and a suction port connectable to a suction source; and a closure member normally disposed in an open position spaced below the suction port but movable to a closed position against the suction port when the container is full to prevent passage of fluid from the container to the suction source; said closure member being supported on a stem passing through an opening in said top wall of the container adjacent to but laterally of said suction port; said stem passing through an opening in said closure member and being formed with an enlargement at its lower end normally supporting the closure member in its open position spaced below said suction port; said fluid inlet port being connected to a tube extending internally of the container to direct inletted fluid downwardly therethrough while minimizing splash, said tube being formed with a slot extending continuously for substantially the complete length of the tube within the container enabling air in the inletted fluid to enter the container without bubbling through the fluid therein.

* * * * *